(12) United States Patent
Moody et al.

(10) Patent No.: US 7,029,885 B2
(45) Date of Patent: Apr. 18, 2006

(54) PROCESS FOR THE PREPARATION OF AMPICILLIN

(75) Inventors: Harold M. Moody, Maastricht (NL); Wilhelmus H. J. Boesten, Sittard (NL)

(73) Assignee: DSM IP Assests B.V., Heerlen (NL)

( * ) Notice: Subject to any disclaimer, the term of this patent is extended or adjusted under 35 U.S.C. 154(b) by 58 days.

(21) Appl. No.: 09/457,765

(22) Filed: Dec. 10, 1999

(65) Prior Publication Data

US 2002/0009769 A1 Jan. 24, 2002

Related U.S. Application Data

(63) Continuation of application No. PCT/NL98/00295, filed on May 25, 1998.

(30) Foreign Application Priority Data

Jun. 10, 1997 (NL) .............................................. 1006266

(51) Int. Cl.
*C12N 9/00* (2006.01)

(52) U.S. Cl. ...................................................... 435/183
(58) Field of Classification Search ................. 435/183, 435/43; 424/94.1
See application file for complete search history.

(56) References Cited

FOREIGN PATENT DOCUMENTS

| EP | 0473008 | 3/1992 |
|----|---------|--------|
| FR | 2188608 | 1/1974 |
| WO | 9201061 | 1/1992 |
| WO | 9503420 | 2/1995 |
| WO | 9602663 | 2/1996 |
| WO | 9630376 | 10/1996 |
| WO | WO 99/15531 | 4/1999 |
| WO | WO 99/15532 | 4/1999 |
| WO | WO 99/20786 | 4/1999 |

*Primary Examiner*—Michael Meller
(74) *Attorney, Agent, or Firm*—Mayer Brown Rowe & Maw LLP

(57) ABSTRACT

Ampicillin is produced in a batch process by enzymatic acylation of 6-aminopenicillanic acid (6-APA) with the aid of phenylglycine derivative such as D-phenylglycine amide. High conversions of phenylglycine derivative may be achieved by having the total concentration in the reaction mixture of 6-APA and ampicillin greater than 250 mM and the molar ration of total quantity of phenylglycine derivative to total quantity of 6-APA less than 2.5. Higher yields of ampicillin may be achieved when the amount of dissolved 6-APA is kept low, e.g. below 300 mM.

10 Claims, 2 Drawing Sheets

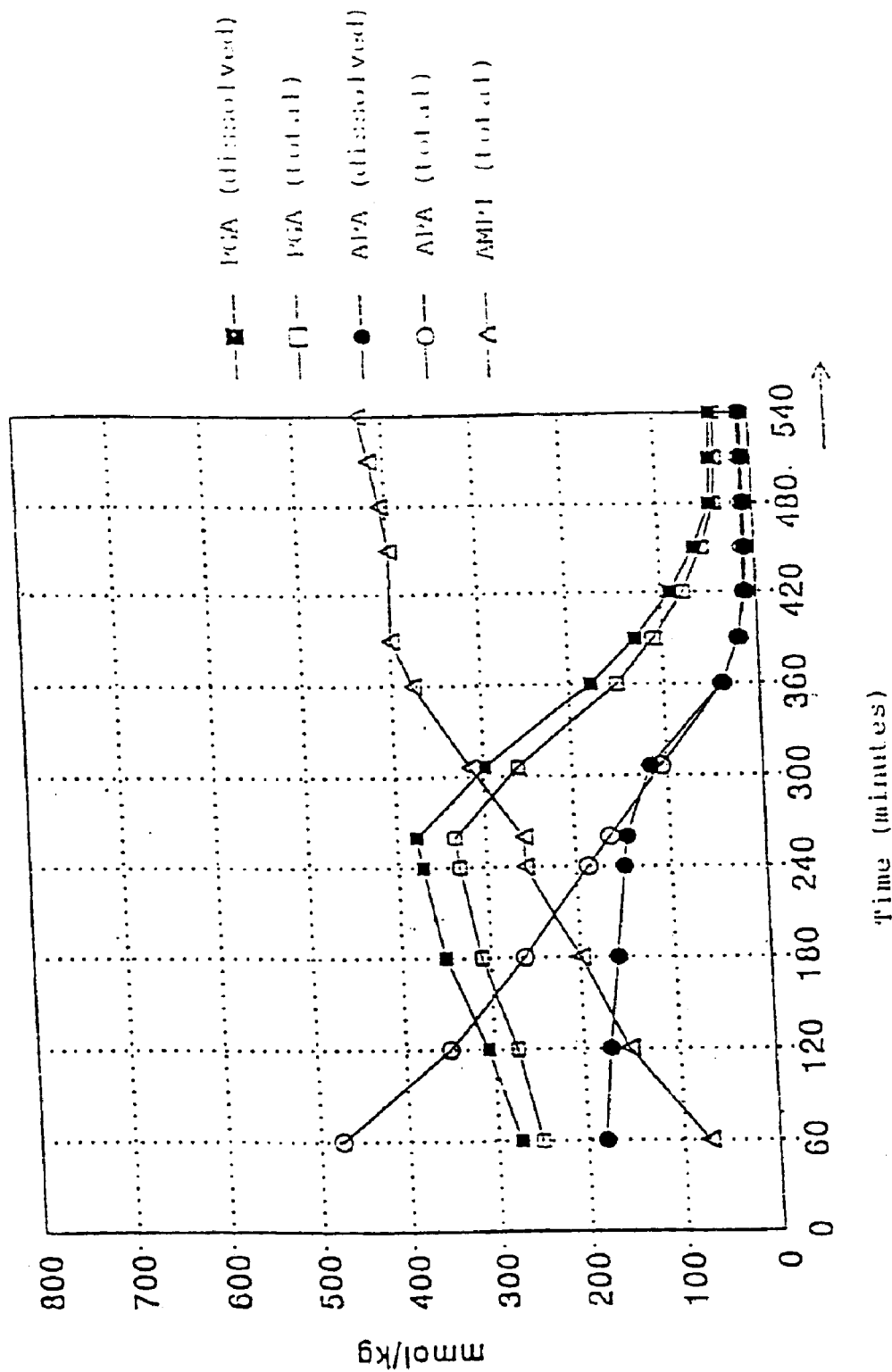

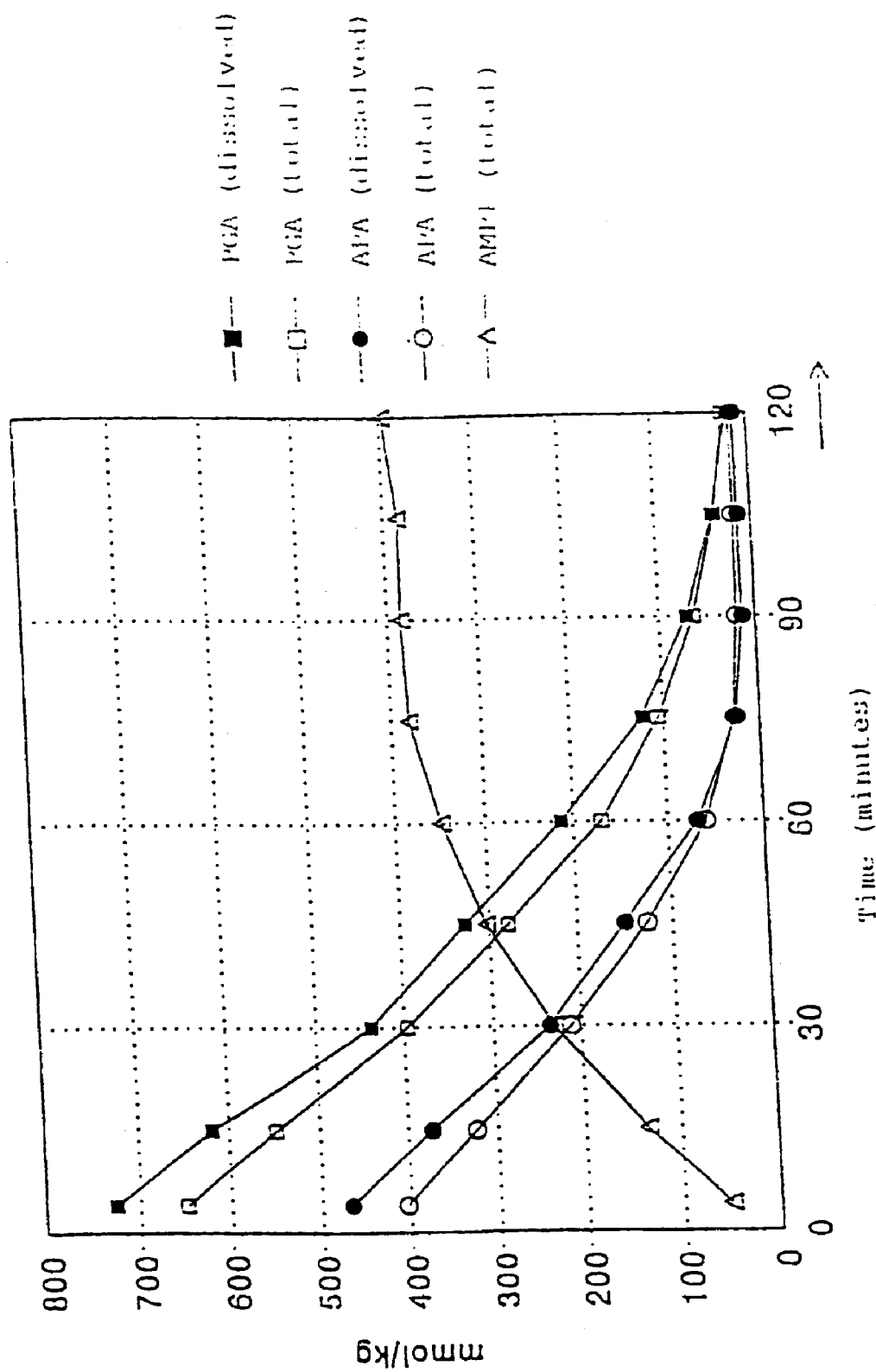

PROCESS FOR THE PREPARATION OF AMPICILLIN

This application is a continuation of PCT/NL98/00295 filed May 25, 1998 which is a continuation of Netherlands 1006266 filed Jun. 10, 1997.

FIELD OF THE INVENTION

The invention relates to a process for the preparation of ampicillin in which 6-aminopenicillanic acid (6-APA) is subjected to an enzymatic acylation reaction with the aid of a phenylglycine derivative, with the total concentration of the 6-APA present in the reaction mixture, plus ampicillin, being greater than 250 mM, the concentration of 6-APA in solution being kept lower than 300 mM and the molar ratio of acylation agent to 6-APA which is employed being less than 2.5.

BACKGROUND OF THE INVENTION

WO-A-92/01061 describes the preparation of β-lactam derivatives, including ampicillin, via enzymatic acylation of a β-lactam nucleus, for example 6-APA, at high concentrations of acylation agent plus β-lactam derivative. The concentration of the β-lactam nucleus is kept relatively low. From the examples it can be deduced that high conversions are achieved at a high molar ratio of acylation agent to β-lactam nucleus, whereas the conversion is significantly lower at a lower molar ratio of acylation agent to β-lactam nucleus. A disadvantage of the use of a high molar ratio of acylation agent to β-lactam nucleus is that large amounts of acylation agent are lost because of hydrolysis of the acylation agent. In addition it has been found that upgrading of ampicillin is hampered by a relatively large quantity of D-phenylglycine, relative to ampicillin, being present in the reaction mixture obtained after the enzymatic acylation reaction, as a result of which a smaller quantity of ampicillin can be isolated.

It has been found that in order to achieve a high conversion in the process it is of great importance to be able to carry out the reaction at high concentrations, and therefore also at a high concentration of β-lactam nucleus.

WO-A-96/02663 describes a process in which the enzymatic acylation reaction of β-lactam nuclei is carried out at a constant concentration of the reactants. In the continuous process described here the aim is to achieve the highest possible level of concentration of both reactants.

It has been found, however, that when the preparation of ampicillin is carried out at a high concentration of 6-APA, only a relatively low conversion is achieved, compared with conversions which could be achieved in the preparation of other β-lactam derivatives, such as cephalexin.

BRIEF SUMMARY OF THE INVENTION

The applicant has now surprisingly found that by ensuring that the concentration of 6-APA in dissolved form present in the reaction mixture is kept relatively low, a higher conversion can be achieved than when the concentration of dissolved 6-APA is chosen to be as high as possible. Furthermore it is found that the stirrability of the reaction mixture is considerably better when the concentration of dissolved 6-APA is kept low.

BRIEF DESCRIPTION OF THE DRAWINGS

Graph 1 shows concentration of reactants and products in the reaction mixture in a process according to the present invention.

Graph 2 shows concentration of reactants and products in the reaction mixture in a process outside of the present invention.

DETAILED DESCRIPTION OF THE INVENTION

In the context of the present invention "conversion" means the molar ratio of ampicillin formed to the quantity of 6-APA employed. The concentration of dissolved 6-APA is expressed as the quantity of 6-APA in moles per kg of reaction mixture; the total concentration, dissolved and undissolved, of 6-APA and ampicillin is expressed as the quantity of 6-APA plus ampicillin in moles per kg of total reaction mixture; apart from the solution, the total reaction mixture may contain a number of solid substances, for example 6-APA, ampicillin, phenylglycine and immobilized enzyme.

The molar ratio of acylation agent to 6-APA, i.e. the total quantity of added phenylglycine derivative divided by the total quantity of added 6-APA, expressed in moles, is less than 2.5. The molar ratio is preferably between 1.0 and 2.0, in particular between 1.2 and 1.8.

The enzymatic acylation reaction is preferably carried out as a batch process. If desired it is also possible to carry out the reaction continuously, with the concentration of dissolved 6-APA being controlled in line.

In the process according to the invention, the total concentration of 6-APA plus ampicillin (in dissolved and in undissolved form) in the reaction mixture is made higher than 250 mM, preferably higher than 300 mM, and in particular higher than 350 mM.

During the preparation of ampicillin, the concentration of dissolved 6-APA is essentially kept lower than 300 mM, preferably lower than 250 mM. At a higher concentration of the acylation agent a higher concentration of dissolved 6-APA can if necessary be chosen than at a lower concentration. This is because the reaction rate is higher at a higher concentration of the acylation agent, which means that 6-APA is present at a high concentration in dissolved form for only a relatively short time.

The concentration of 6-APA present in the reaction mixture in dissolved form can be kept low in various ways. One possibility of keeping the concentration of dissolved 6-APA low is to initially charge only part of the total quantity of 6-APA and add the rest during the reaction. A disadvantage of this, however, is that 6-APA then has to be added as a solid—which creates practical problems. As a result, the total quantity of 6-APA is preferably initially charged in a batch process at the beginning of the reaction, after which, during the enzymatic acylation reaction, the concentration of 6-APA in the reaction mixture will decrease and the concentration of ampicillin will increase. A suitable method of nevertheless achieving a low concentration of dissolved 6-APA is, for example, to keep the pH at a lower value compared with the pH at which a maximum solubility of the reactants is achieved. A particularly suitable method of keeping the concentration of 6-APA in dissolved form low is, for example, to ensure that the concentration of the phenylglycine derivative is kept low, for example by metering in the phenylglycine derivative partially in the course of the reaction.

It has in fact been found that when the phenylglycine derivative concentration is kept low, little 6-APA goes into solution, so that the concentration of 6-APA in solution can be controlled by metering in the phenylglycine derivative.

Phenylglycine in activated form, for example an amide or an ester, in particular a methyl ester, can be used as the acylation agent in the (enzymatic) acylation reaction. D-phenylglycine amide (PGA) is preferably used.

A particularly suitable embodiment is obtained when PGA is added in the form of a salt thereof, preferably the salt of PGA and a mineral acid, for example PGA.HCl, PGA.1/2H$_2$SO$_4$ and PGA.HNO$_3$. In this way it is in fact possible in a simple way to achieve optimum metering of the PGA by keeping the pH constant. PGA.1/2H$_2$SO$_4$ is preferably used, because this salt has a very high solubility.

The temperature at which the enzymatic acylation reaction is carried out is generally lower than 40° C., preferably between −5 and 35° C. The pH at which the enzymatic acylation reaction is carried out is generally between 5.5 and 8.0, preferably between 6.0 and 6.8.

Any enzyme that is suitable as a catalyst in the linking reaction can in principle be used as the enzyme. Such enzymes are for example the enzymes which are known under the general name penicillin amidase or penicillin acylase. Such enzymes are described in for example J. G. Shewale et al., Process Biochemistry, August 1989, pp. 146–154, and in J. G. Shewale et al., Process Biochemistry International, June 1990, pp. 97–103. Examples of suitable enzymes are enzymes derived from *Acetobacter*, in particular *Acetobacter pasteurianum*, *Aeromonas*, *Alcaligenes*, in particular *Alcaligenes faecalis*, *Aphanocladium*, *Bacillus* sp., in particular *Bacillus megaterium*, *Cephalosporium*, *Escherichia*, in particular *Escherichia coli*, *Flavobacterium*, *Fusarium*, in particular *Fusarium oxysporum* and *Fusarium solani*, *Kluyvera*, *Mycoplana*, *Protaminobacter*, *Proteus*, in particular *Proteus rettgari*, *Pseudomonas* and *Xanthomonas*, in particular *Xanthomonas citrii*.

An immobilized enzyme is preferably used since the enzyme can then be simply separated off and re-used. A suitable immobilization technology is described in for example EP-A-222462. Another suitable technology involves immobilizing the Penicillin G acylase on a carrier which contains a gelling agent, for example gelatin, and a polymer with free amino groups, for example alginate amine, chitosan or polyethylenimine. In addition, enzymes in crystalline form (CLEC's™) can also be used.

Of the immobilized enzymes which are commercially available, those which were found to be particularly suitable were, for example, the *Escherichia coli* enzyme from Boehringer Mannheim GmbH which is commercially available under the name Enzygel®, the immobilized Penicillin-G acylase from Recordati and the immobilized Penicillin-G acylase from Pharma Biotechnology, Hannover.

The (enzymatic) acylation reaction and the further upgrading of the reaction mixture are in practice usually carried out in water. If desired, the reaction mixture can also contain an organic solvent or a mixture of organic solvents, preferably less than 30 vol %. Examples of organic solvents which can be used are alcohols with 1–7 C atoms, for example a monoalcohol, in particular methanol or ethanol; a diol, in particular ethyleneglycol; or a triol, in particular glycerol.

The reaction is preferably almost completely stopped when near to maximum conversion has been achieved. A suitable embodiment for achieving this is to lower the pH, preferably to a value between 4.0 and 6.3, in particular between 5.0 and 5.7. Another suitable embodiment is to lower the temperature of the reaction mixture as soon as maximum conversion is achieved. A combination of the two embodiments is also possible.

After the reaction has been almost stopped on achieving maximum conversion, the reaction mixture is usually present in the form of a suspension which contains several solid substances, for example ampicillin, D-phenylglycine and immobilized enzyme. For the sake of process economics, the immobilized enzyme is preferably recovered. A suitable way of doing this is, for example, to filter the reaction mixture through a screen, while stirring, with the direction of rotation of the agitator being preferably such that the suspension is pumped upwards in the centre of the agitator. Valuable components, for example AMPI and PG, can subsequently be recovered; for example with the aid of a pH shift. The mother liquor which remains contains only a few byproducts, and can subsequently be recirculated if desired.

In the context of the present invention, the various components can be present in the reaction mixture either in free form or as salts. The stated pH value always means the pH value measured with a pH electrode calibrated at room temperature.

The invention will be further explained by means of the examples, without, however, being limited thereto.

Abbreviations:
AMPI.3H$_2$O=ampicillin trihydrate
6-APA=6-aminopenicillanic acid
PGA=D-phenylglycine amide
PG=D-phenylglycine
Assemblase™ is an immobilized *Escherichia coli* penicillin acylase from *E. coli* ATCC 1105, as described in WO-A-97/04086. The immobilization has been carried out as described in EP-A-222462, with gelatin and chitosan being used as gelling agent and glutaraldehyde as cross-linker. The final activity of the *Escherichia coli* penicillin acylase is determined by the amount of enzyme which has been added to the activated globules, and amounted to 3 ASU/g of dry weight, with 1 ASU (Amoxicillin Synthesis Unit) being defined as the amount of enzyme which generates 1 g of Amoxicillin.3H$_2$O per hour from 6-APA and D-p-hydroxyphenylglycine methyl ester (HPGM) (at 20° C.; 6.5% of 6-APA and 6.5% of HPGM).

EXAMPLE I

Preparation of PGA.1/2H$_2$SO$_4$ Solution.

301.6 g of PGA (2.00 mol) was suspended in 650 g of water at T=5° C. 102.1 g of 96% H$_2$SO$_4$ (1.00 mol) was added dropwise over a period of 1 hour, with stirring, with the temperature being kept at T<25° C. by cooling.

EXAMPLE II

Synthesis of Ampicillin

An enzyme reactor (1.5 l, diameter 11 cm), fitted with a screen bottom with a 175 μm mesh, was filled with 300 g net wet Assemblase⁶.

A preparation reactor (1.2 l) was filled with 131.6 g of 6-APA (0.600 mol), 30.2 g of PGA (0.200 mol) and 400 ml of water (T=10° C.). This mixture was stirred for 15 minutes at T=10° C. and then transferred to the enzyme reactor at time t=0 with 100 ml of water (T=10° C.).

At t=0 the agitator in the enzyme reactor was started. Over a period of 283 minutes 423.7 g (0.800 mol) of PGA.1/2H$_2$SO$_4$ solution was added at a constant rate, with the temperature being kept at 10° C. The pH was about 6.3. From t=328 minutes onwards the pH was kept at 6.3 by titration with 6N (aqueous) H$_2$SO$_4$. At t=540 minutes the quantity of Ampicillin was at a maximum and the pH was reduced to 5.6 by adding 6N H$_2$SO$_4$.

The enzyme reactor now contained:
575 mmol of AMPI (=96% relative to the amount of 6-APA used)

15 mmol of 6-APA
50 mmol of PGA
365 mmol of PG

The concentrations during the reaction are shown in Graph 1.

Comparative Experiment A

Synthesis of Ampicillin

An enzyme reactor (1.5 l, diameter 11 cm), fitted with a screen bottom with a 175 μm mesh, was filled with 300 g net wet Assemblase[6].

A preparation reactor (1.2 l) was filled with 143.2 g (0.950 mol) of PGA in 500 ml of water at 10° C. Over a period of 15 minutes 131.6 g of 6-APA (0.600 mol) was added in small portions at 10° C., with cooling, while the pH was kept at 7.0 by titration with 6N (aqueous) $H_2SO_4$. A total of 54.5 ml of 6N $H_2SO_4$ was needed. The mixture was stirred for 15 minutes at T=10° C. and then transferred to the enzyme reactor at time t=0 with 100 ml of water (T=10° C.). At t=0 the agitator in the enzyme reactor was started. The pH was kept at 7.0 by titration with 6N $H_2SO_4$. The temperature was kept at 10° C. At t=160 minutes the quantity of Ampicillin was at a maximum and the pH was reduced to 5.6 by means of 6N $H_2SO_4$. A total of 147.6 ml of 6N $H_2SO_4$ was added to the enzyme reactor. The mixture was relatively viscous and difficult to stir.

The enzyme reactor now contained:
 551 mmol of AMPI (=92% relative to the amount of 6-APA used)
 24 mmol of 6-APA
 50 mmol of PGA
 330 mmol of PG The concentrations during the reaction are shown in Graph 2.

What is claimed is:

1. A process for preparation of ampicillin comprising:
  acylating 6-aminopenicillanic acid (6-APA) with a phenylglycine derivative and an enzyme to form a reaction mixture wherein the process is carried out while
   i) the total concentration in the reaction mixture of 6-APA and ampicillin combined is substantially throughout the reaction, greater than 250 mM;
   ii) metering in partially the 6-APA and/or the phenylglycine derivative in the course of the acylation reaction to thereby maintain the concentration of dissolved 6-APA lower than 300 mM throughout the reaction; and
   iii) the molar ratio of the total quantity of phenylglycine derivative to the total quantity of 6-APA is less than 2.5.

2. Process according to claim 1, wherein the acylation reaction is carried out while the total concentration of the 6-APA and ampicillin present in the reaction mixture is, substantially throughout the reaction, greater than 300 mM.

3. Process according to any one of claims 1 or 2, wherein the acylation reaction is carried out while metering in partially the 6-APA and/or the phenylglycine derivative to thereby maintain the concentration of dissolved 6-APA lower than 250 mM throughout the reaction.

4. Process according to claim 1, wherein the acylation reaction is carried out while the molar ratio of the total quantity of phenylglycine derivative to the total quantity of 6-APA is less than 2.0.

5. Process according to claim 1, wherein the phenylglycine derivative is metered in as a salt of D-phenylglycine amide and an acid.

6. Process according to claim 5, wherein the phenylglycine derivative is metered in the form of a solution of D-phenylglycine amide, 1/2 $H_2SO_4$ in water.

7. Process according to claim 1, which comprises charging a portion of the total amount of 6-APA to the reaction mixture at the beginning of the reaction such portion providing a concentration of dissolved 6-APA less than 300 mM and introducing the remainder of the total amount during the remainder of the acylation reaction to maintain the concentration of dissolved 6-APA less than 300 mM.

8. Process according to claim 7, wherein the concentration of dissolved 6-APA is kept lower than 250 mM throughout the acylation reaction.

9. Process according to claim 8, wherein the total concentration of the 6-APA and ampicillin present in the reaction mixture is, substantially throughout the acylation reaction, greater than 300 mM.

10. A process for the preparation of ampicillin by acylating a quantity of 6-aminopenicillanic acid (6-APA) with a quantity of phenylglycine derivative and an enzyme in an aqueous reaction medium to provide a reaction mixture containing dissolved 6-APA; said process comprising
  initially introducing a part of said quantity of the 6-APA and/or a part of the quantity of phenylglycine derivative into the reaction medium under conditions allowing ampicillin to be formed by the acylation reaction and,
  thereafter adding the rest of the quantity of 6-APA and/or phenylglycine derivative, under conditions whereby ampicillin will continue to be formed by the acylation reaction, and
  wherein the concentration of dissolved 6-APA in the reaction mixture is, throughout the acylation reaction, lower than 300 mM and the total combined concentrations in the reaction mixture of 6-APA and formed ampicillin is greater than 250 mM; and further
  wherein the molar ratio of the quantity of phenylglycine derivative to the quantity of 6-APA is less than 2.5.

* * * * *